United States Patent
Tohme et al.

(10) Patent No.: US 10,733,770 B2
(45) Date of Patent: Aug. 4, 2020

(54) SYSTEM AND METHOD FOR PERFORMING FAULT-TOLERANT RECONSTRUCTION OF AN IMAGE

(71) Applicant: GENERAL ELECTRIC COMPANY, Schenectady, NY (US)

(72) Inventors: Michel Souheil Tohme, Waukesha, WI (US); Floribertus P. Heukensfeldt Jansen, Ballston Lake, NY (US); Timothy Wayne Deller, Elm Grove, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 92 days.

(21) Appl. No.: 15/883,672

(22) Filed: Jan. 30, 2018

(65) Prior Publication Data

US 2018/0308262 A1    Oct. 25, 2018

Related U.S. Application Data

(60) Provisional application No. 62/488,345, filed on Apr. 21, 2017.

(51) Int. Cl.
*G06T 11/00* (2006.01)
*A61B 6/00* (2006.01)
*A61B 6/03* (2006.01)

(52) U.S. Cl.
CPC ............ *G06T 11/005* (2013.01); *A61B 6/037* (2013.01); *A61B 6/5258* (2013.01); *A61B 6/5282* (2013.01); *G06T 2210/41* (2013.01)

(58) Field of Classification Search
CPC . G06T 11/005; G06T 2210/41; A61B 6/5258; A61B 6/037; A61B 6/5282
See application file for complete search history.

(56) References Cited

U.S. PATENT DOCUMENTS

| | | | | |
|---|---|---|---|---|
| 4,178,510 A | * | 12/1979 | Wagner | A61B 6/032 378/51 |
| 5,384,699 A | | 1/1995 | Levy et al. | |
| 6,307,203 B1 | * | 10/2001 | Stearns | G01T 1/172 250/363.03 |
| 6,919,568 B2 | * | 7/2005 | Odogba | A61B 6/585 250/336.1 |

(Continued)

OTHER PUBLICATIONS

Hugo W.A.M. De Jong, et al.; Correction Methods for Missing Data in Sinograms of the HRRT PET Scanner; IEEE Transactions on Nuclear Science, vol. 50, No. 5, Oct. 2003.

(Continued)

*Primary Examiner* — Brenda C Bernardi
(74) *Attorney, Agent, or Firm* — Grogan, Tuccillo & Vanderleeden, LLP

(57) ABSTRACT

A method for performing fault-tolerant reconstruction of an image of an object is provided. The method includes acquiring a dataset corresponding to the object via a plurality of sensors, and detecting anomalous data within the dataset based at least in part on a statistical difference between the anomalous data and reference data within the dataset. The anomalous data is acquired by at least a first sensor of the plurality, and the reference data is acquired by at least a second sensor of the plurality that neighbors the first sensor.

17 Claims, 7 Drawing Sheets

(56) References Cited

U.S. PATENT DOCUMENTS

| | | | | |
|---|---|---|---|---|
| 7,142,636 B2* | 11/2006 | Hsieh | ............... | A61B 6/032 |
| | | | | 378/98.8 |
| 7,602,951 B2* | 10/2009 | Hsieh | ............... | G06T 11/005 |
| | | | | 382/128 |
| 8,158,951 B2* | 4/2012 | Bal | ............... | G01T 1/247 |
| | | | | 250/370.09 |
| 8,450,693 B2 | 5/2013 | Stearns | | |
| 9,195,899 B2* | 11/2015 | Topfer | ............... | G06K 9/38 |
| 2003/0014132 A1* | 1/2003 | Ohba | ............... | G01T 1/2985 |
| | | | | 700/31 |
| 2010/0116994 A1* | 5/2010 | Wollenweber | ............... | G01T 1/1611 |
| | | | | 250/363.03 |
| 2019/0361136 A1* | 11/2019 | Song | ............... | A61B 6/037 |

OTHER PUBLICATIONS

Brigitte Gundlich, et al.; Compensation Strategies for PET Scanners with Unconventional Scanner Geometry; 2005 IEEE Nuclear Science Symposium Conference Record.

Uygar Tuna, et al.; Gap-Filling for the High-Resolution PET Sinograms With a Dedicated DCT-Domain Filter; IEEE Transactions on Medical Imaging, vol. 29, No. 3, Mar. 2010.

* cited by examiner

SYSTEM AND METHOD FOR PERFORMING FAULT-TOLERANT RECONSTRUCTION OF AN IMAGE

CROSS-REFERENCE TO RELATED APPLICATIONS

This application claims priority to and the benefit of, U.S. Provisional Pat. App. Ser. No. 62/488,345, filed Apr. 21, 2017, the disclosure of which is incorporated herein by reference in its entirety.

BACKGROUND

Technical Field

Embodiments of the invention relate generally to imaging systems, and more specifically, to a system and method for performing fault-tolerant reconstruction of an image of an object.

Discussion of Art

Positron Emission Tomography ("PET") imaging is a non-invasive nuclear imaging technique that involves the creation of tomographic images from positron emitting radionuclides injected into a subject of interest. In many PET imaging systems, a radionuclide-labeled agent is administered to the subject while positioned within a detector ring. As the radionuclides decay, positively charged anti-electrons known as "positrons" are emitted therefrom. As these positrons travel through the tissues of the subject, they lose kinetic energy and ultimately combine with an electron, resulting in mutual annihilation. The positron annihilation results in a pair of oppositely directed annihilation photons, e.g., gamma rays, being emitted at approximately 511 keV, which are subsequently detected by PET detectors/sensors, i.e., scintillators such as crystals, within the detector ring. When struck by an annihilation photon, each PET detector converts the energy of the photon into a burst of light photons of lower energy; this burst of light is then detected by a photovoltaic component such as a photodiode.

The signals from the photovoltaics are processed as incidences of annihilation photons typically referred to as "PET events." When two PET events occur at oppositely positioned PET detectors at approximately the same time, a "coincidence" is registered. Data sorting units process the coincidences to determine true coincidence events and to sort out data representing dead times and single gamma ray detections. The coincidence events are binned and integrated to form frames of PET data, which may be reconstructed into images depicting the distribution of the radionuclide-labeled agent and/or metabolites thereof in the subject.

Many PET detectors, however, are subject to various modes of failure that typically generate artifacts and/or quantitative inaccuracies in reconstructed images, which in turn may result in false and/or inconclusive diagnosis. For example, PET detector failures may cause one or more of the following errors: insufficient counts for a PET detector; excessive counts for a PET detector; and/or misplaced counts for a PET detector, i.e., where a gamma ray strikes one PET detector, but is recorded against a different PET detector.

While some PET imaging systems seek to correct the effects of PET detector failures, such PET imaging systems typically are able to only detect and correct for intermittent PET detector failures that occur when a PET detector "flickers", i.e., toggles between providing good data and no data. Moreover, many such PET imaging systems require the PET data to be acquired and/or stored in what is known as "List Mode," which often entails storing coincidences in chronological order within an array for the purpose of calculating a fractional weight of valid PET data with respect to a period of time. This approach, however, is limited to correcting the very specific type of PET detector failure, mentioned above, in which a PET detector is either working perfectly or providing no data.

As such, there exist types of PET detector failures that can corrupt PET data while typically going undetected by prior art PET imaging systems. For example, many PET imaging systems usually fail to detect and/or correct for corrupted detector crystal maps, large energy gain errors, false detector triggering causing significant detector dead time, and/or time stamp corruption.

What is needed, therefore, is an improved system and method for performing fault-tolerant reconstruction of an image of an object.

BRIEF DESCRIPTION

In an embodiment, a method for performing fault-tolerant reconstruction of an image of an object is provided. The method includes acquiring a dataset corresponding to the object via a plurality of sensors, and detecting anomalous data within the dataset based at least in part on a statistical difference between the anomalous data and reference data within the dataset. The anomalous data is acquired by at least a first sensor of the plurality, and the reference data is acquired by at least a second sensor of the plurality that neighbors the first sensor.

In another embodiment, a system for performing fault-tolerant reconstruction of an image of an object is provided. The system includes a plurality of sensors and a controller. The plurality of sensors is operative to acquire a dataset corresponding to the object. The controller is in electronic communication with the plurality of sensors and operative to detect anomalous data within the dataset based at least in part on a statistical difference between the anomalous data and reference data within the dataset. The anomalous data is acquired by at least a first sensor of the plurality, and the reference data is acquired by at least a second sensor of the plurality that neighbors the first sensor.

In yet another embodiment, a non-transitory computer readable medium storing instructions is provided. The stored instructions are configured to adapt a controller to detect anomalous data within a dataset based at least in part on a statistical difference between the anomalous data and reference data within the dataset. The dataset corresponds to an object and is acquired by a plurality of sensors. The anomalous data is acquired by at least a first sensor of the plurality, and the reference data is acquired by at least a second sensor of the plurality that neighbors the first sensor.

DRAWINGS

The present invention will be better understood from reading the following description of non-limiting embodiments, with reference to the attached drawings, wherein below:

DETAILED DESCRIPTION

Figure 1:
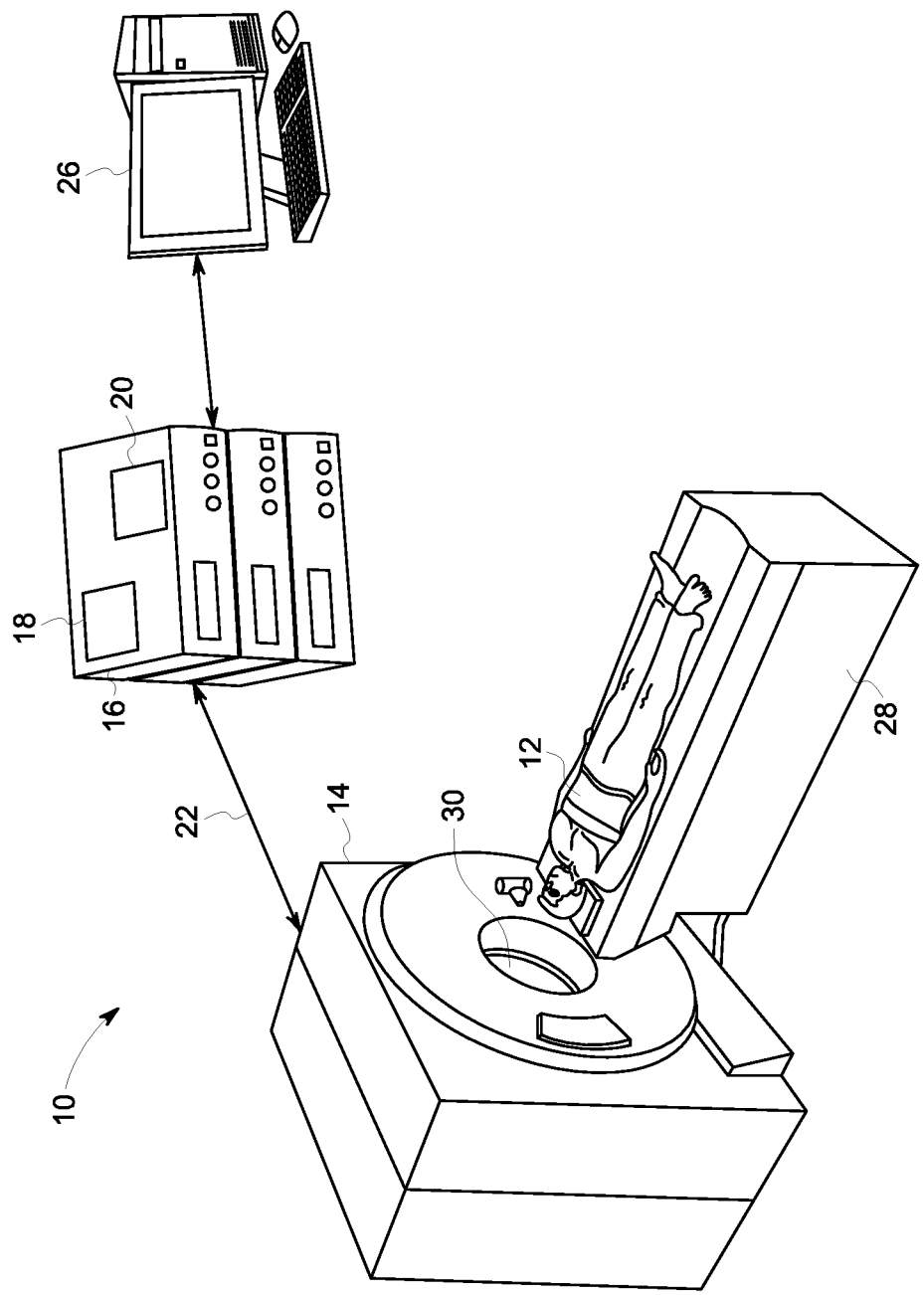
FIG. 1 is a block diagram of an exemplary system for performing fault-tolerant reconstruction of an image of an object, in accordance with an embodiment of the present invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components, such as a fiber optical connection, may be present. The term "real-time," as used herein, means a level of processing responsiveness that a user senses as sufficiently immediate or that enables the processor to keep up with an external process.

Further, while the embodiments disclosed herein are described with respect to PET imaging systems, it is to be understood that embodiments of the present invention may be applicable to other Nuclear Medicine ("NM") imaging systems, e.g., Single Photon Emission Computed Tomography ("SPECT"); MRI systems; Computed Tomography ("CT") imaging systems; ultrasound imaging systems; and imaging systems which utilize more than one detector/sensor or view to reconstruct an image of an object, i.e., a photosensitive chip within a digital camera. Further still, as will be appreciated, embodiments of the present invention related imaging systems may be used to analyze tissue generally and are not limited to human tissue.

Referring now to FIG. 1, the major components of a PET imaging system 10 for performing fault-tolerant reconstruction of an image of an object/patient/subject 12, in accordance with an embodiment of the present invention, is shown. As will be understood, while the system 10 is depicted in the accompanying drawings as a combined PET/CT imaging system, as stated above, in embodiments, the PET imaging system 10 may be a standalone PET imaging system or combined with another type of imaging system, e.g., PET/MRI. Accordingly, as shown in FIG. 1, the system 10 includes a detector assembly 14 that is utilized to scan the patient 12, and a controller 16, which includes at least one processor 18 and a memory device 20. The controller 16 may electronically communicate with the detector assembly 14 via one or more communication links 22 over which emission data generated by a plurality of PET detector elements/sensors 24 (FIG. 2) disposed within the detector assembly 14 may be passed to the controller 16. As will be appreciated, in embodiments, the number of communication links 22 may correspond to the number of sensors 24, e.g., n sensors 24 and at least n communication links 22. The system 10 may further include a human-machine interface ("HMI") 26, i.e., a work station, that provides for a user/technologist/physician to interact with the system 10. The system 10 may further include a gantry/table 28 for supporting the patient 12 during scanning procedures.

As will be appreciated, in embodiments, the sensors 24 may be disposed within the detector assembly 14 as a ring (best seen in FIG. 2), referred to hereinafter also as a "detector ring" or "sensor ring," and the detector assembly 14 may have an open cylindrical shape, i.e., a "doughnut," with a central opening 30 which the patient 12 is moved in and out of via the table 28.

Figure 2:
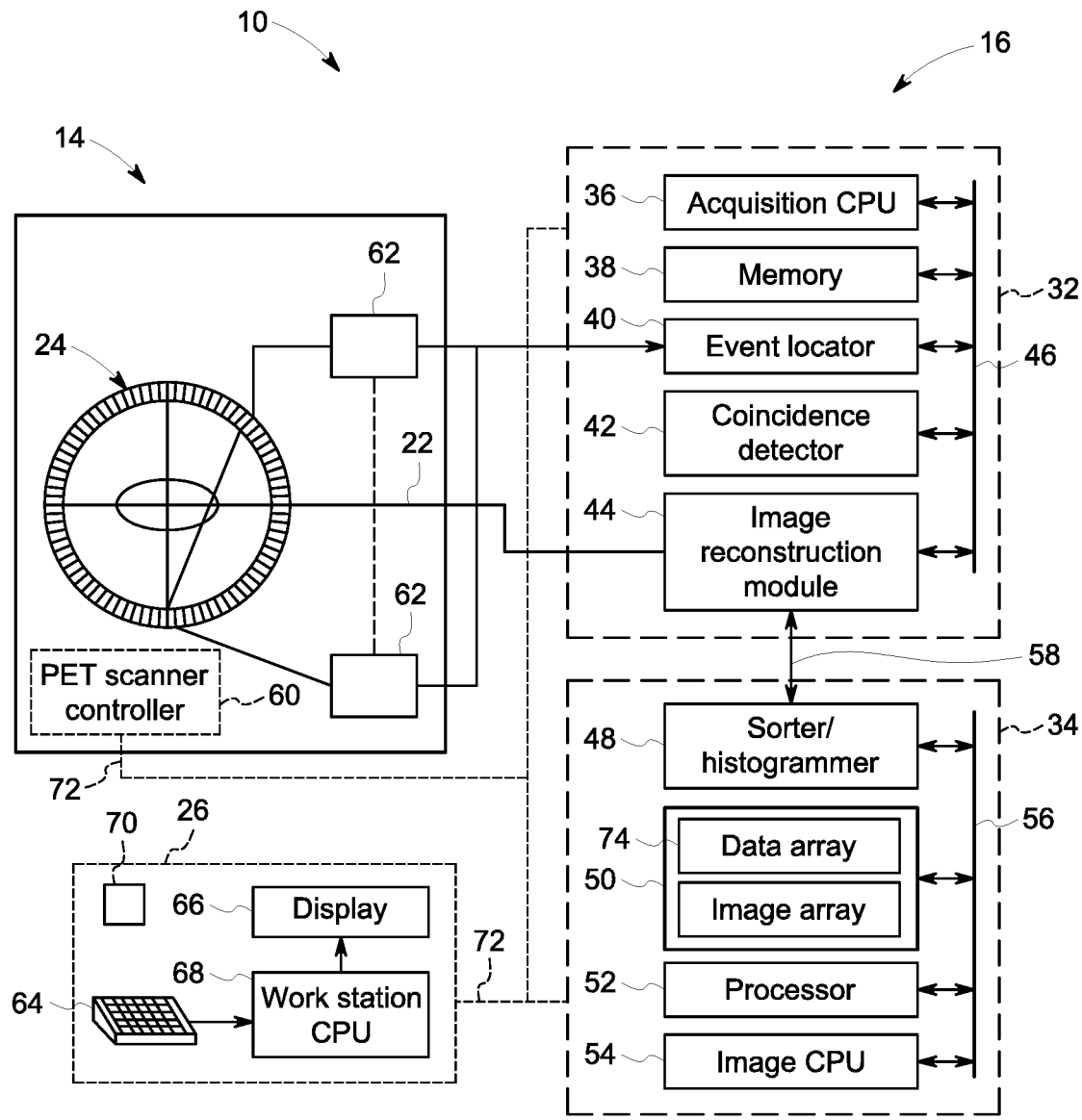
FIG. 2 is a bock diagram of the system of FIG. 1, in accordance with an embodiment of the present invention.

As shown in FIG. 2, the controller 16 may include a data acquisition sub-controller 32 and an image reconstruction module/processor 34. The data acquisition sub-controller 32 may include an acquisition CPU 36, a memory device 38, an event locator module 40, a coincidence detector module 42, and an image reconstruction module 44, which may electronically communicate with each other via a back-plane bus 46. The image reconstruction processor 34 includes a sorter/histogrammer module 48, a memory device 50, an array processor 52, and/or an image processor 54, which may electronically communicate which each other via back-plane bus 56 and with the data acquisition sub-controller 32 via communication link 58.

The detector assembly 14 may further include a PET scan sub-controller 60 and one or more acquisition circuits 62.

The HMI interface 26 may include an input device 64, e.g., a keyboard, mouse, etc., a display screen 66, a processor 68, and/or a memory device 70, and may electronically communicate with the PET scanner controller 60, data acquisition sub-controller 32, and/or the image reconstruction processor 34 via communication link 72.

During operation of the system 10, in accordance with an embodiment, the patient 12 is injected with a radionuclide-labeled agent and positioned within the central opening 30. As positrons are emitted from the radionuclide-labeled agent, they eventually annihilate with electrons to produce/generate gamma rays/photons having energies of about 511 keV. Specifically, each positron/electron annihilation generates two gamma rays having generally opposite velocities, and under ideal conditions, i.e., in the absence of scattering and/or other attenuation effects, are detected nearly simultaneously by two oppositely disposed sensors 24, i.e., a single annihilation event may result in two (2) PET events occurring at approximately the same time to form a coincidence. The location of the annihilation event that generated a coincidence can be derived from lines of response ("LORs") corresponding to the two gamma rays that generated the coincidence.

Accordingly, as PET events occur/are detected by the sensors 24, the acquisition circuits 62 receive signals, e.g., analog voltages, generated by the sensors 24 in response to detecting the gamma rays. As will be appreciated, the signals convey three-dimensional ("3D") positional information and total energy for each gamma ray of each PET event, and the acquisition circuits 62 may produce an event detection pulse that indicates the time/moment the PET events were detected. The signals are then transmitted through the communication links 22 to the data acquisition sub-controller 32, which performs various data enhancing techniques on the signals prior to transmitting the signals to the image reconstruction processor 34.

For example, in embodiments, the signals received by the data acquisition sub-controller 32 from the acquisition circuits 62 may be sent to the event locator module 40, which in turn processes the 3D positional and total energy information of the gamma rays to identify valid PET events. As will be appreciated, in embodiments, the event locator module 40 may determine the exact sensor 24 that detected a particular PET event, and then transmit information, e.g., location, energy, detecting sensor 24 identifier, and/or other information regarding the valid PET event, within an event data packet that is sent to the coincidence detector module 42 and/or image reconstruction module 44.

The coincidence detector module 42 receives event data packets from the event locator module 40 and determines if any two valid PET events form a coincidence, i.e., there is a probability, which in embodiments may be a high probability, that the two valid PET events were generated by gamma rays from the same positron/electron annihilation. Coincident PET event pairs are then recorded as a dataset 74 that corresponds to the object 12, which is then communicated to the image reconstruction module 44. In embodiments, the dataset 74 may be stored in one or more of the memory devices 38, 50, and/or 70.

After having been processed by the image reconstruction module 44, the dataset 74 is electronically communicated to the sorter/histogrammer module 48, which generates a histogram and/or other data structure capable of readily conveying statistical data of the dataset 74. In embodiments, the histogram may be stored as a data array within memory device 50, and accessed by the image processor 54, which reconstructs one or more images of the object 12 based on the dataset 74. In embodiments, the dataset and/or histogram 74 may be/include an array having a plurality of indices each corresponding to a different combination/pair of sensors 24, wherein the value of the array at a particular index represents data corresponding to the two sensors 24, e.g., PET events, coincidence count, etc. As will be appreciated, in embodiments, the coincidence count at an index of the array may be the total number of coincidences for the corresponding pair of sensor 24 during an image frame, which as used herein, refers to the length of time that PET data was collected to generate a single image of the one or more images. As will be understood, such images may be individual still images and/or form part of a series of moving images. Accordingly, in embodiments, the dataset 74 may be at least one of a coincidence count detector map, a singles map, a coincidence-qualified singles count detector map, and a block busy map. The one or more images may then be electronically communicated to the display screen 66 on the HMI 26 for viewing by a technologist and/or physician.

Figure 3:
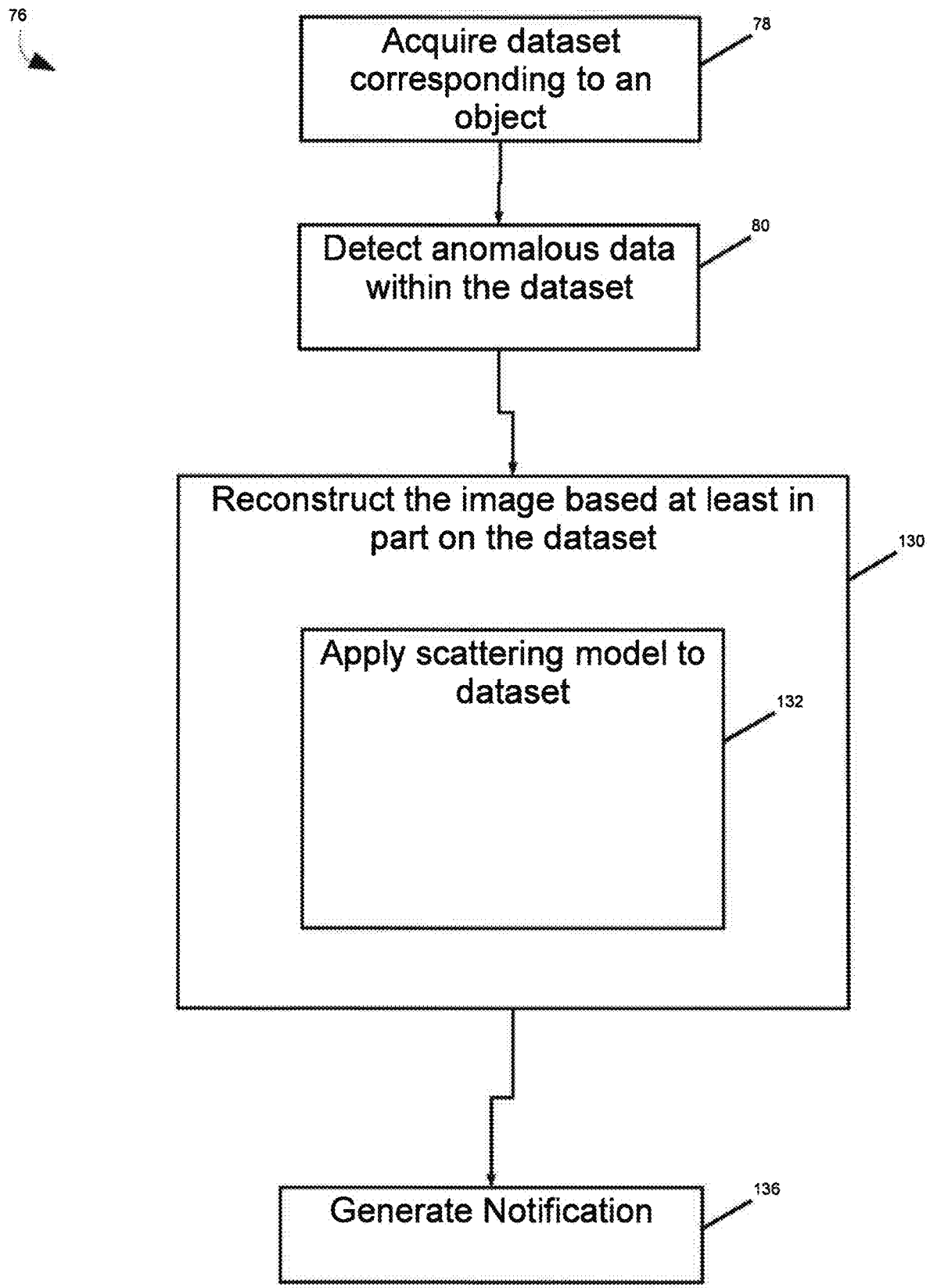
FIG. 3 is a flow chart depicting a method for performing fault-tolerant reconstruction of an image of an object utilizing the system of FIG. 1, in accordance with an embodiment of the present invention.

Turning now to FIG. 3, a method 76 for performing fault-tolerant reconstruction of an image of the object 12 is shown. The method 76 includes acquiring 78 the dataset 74 via the plurality of sensors 24, and detecting 80 anomalous data 82 (FIGS. 6 and 7) within the dataset 74 based at least in part on a statistical difference 84 (FIG. 7) between the anomalous data 82 and reference data 86 (FIGS. 6 and 7) within the dataset 74. As will be appreciated, the anomalous data 82 is acquired by at least a first sensor 88 (FIG. 5) of the plurality 24, and the reference data 86 is acquired by at least a second sensor 90 (FIG. 5) of the plurality that neighbors the first sensor 88. As used herein, "anomalous data" refers to data that may indicate that a sensor 88 has failed and/or is otherwise providing faulty data. The term "reference data," as used herein, refers to data from one or more sensors 90 that serves as a baseline to which the anomalous data 82 can be compared to in order to determine if the sensor(s) 88 from which the anomalous data 82 was acquired by has indeed failed. Accordingly, in embodiments, the statistical difference 84 may be a variation in the number of coincidence counts between the first sensor 88 and the second sensor 90, e.g., the first sensor 88 may have a statically abnormally high or statically abnormally low number of coincidence counts as compared to the second sensor 90.

Figure 4:
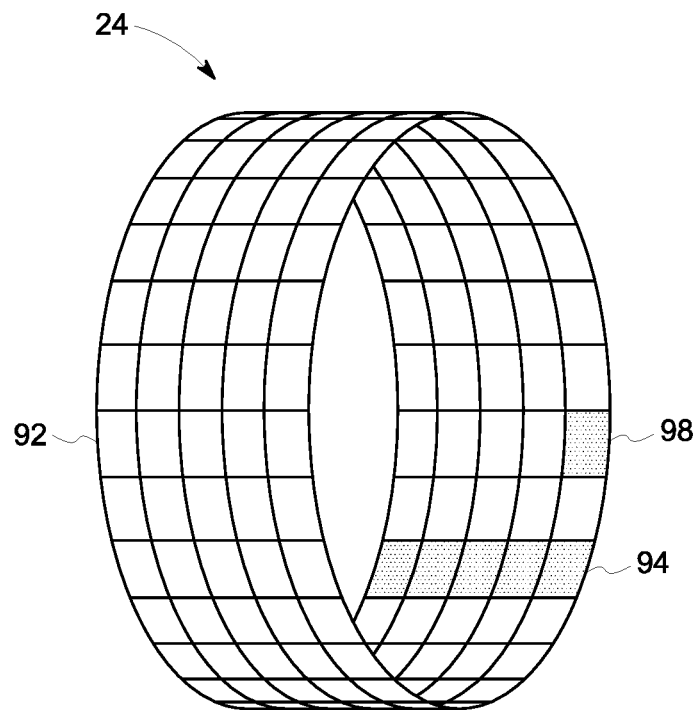
FIG. 4 is a diagram of a detector ring of the system of FIG. 1, in accordance with an embodiment of the present invention.
Figure 5:
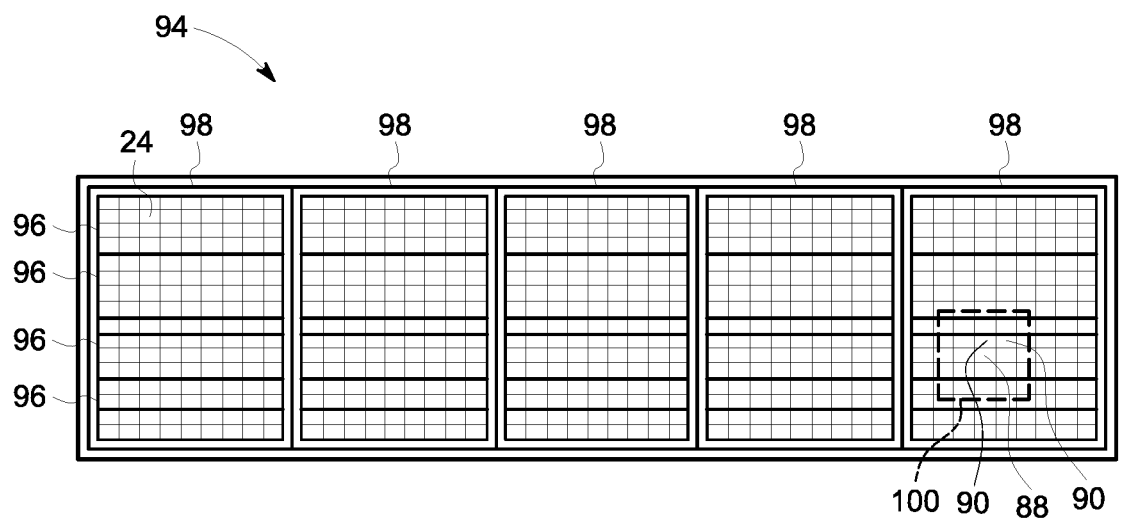
FIG. 5 is a diagram of a module of the detector ring of the system of FIG. 1, in accordance with an embodiment of the present invention.

Referring now to FIGS. 4 and 5, as stated above, the sensors 24 may form a detector ring 92 (shown coiled up in FIG. 4) having one or more modules 94 (best seen in FIG. 5). In such embodiments, the sensors 24 may be grouped within the modules 94 in blocks 96, which may in turn be grouped into units 98. For example, the ring 92 may include twenty-eight (28) modules 94 each including five (5) units 98, with each unit 98 including four (4) 4×9 blocks 96 of sensors 24. As will be appreciated, each of the sensors 24 has a "neighborhood" 100 (FIG. 5), which as used herein, refers to a localized area of sensors 24 surrounding a particular sensor 24. For example, the neighborhood 100 of sensor 88 is shown in FIG. 5 as being a localized area defined as all of the sensors 24 within two sensors 24 from the sensor 88. As will be appreciated, the neighborhood 100 of a sensor 24 may be defined as a radius of any number of sensors 24 from the sensor 24 that defines the center of the neighborhood 100, and/or in other appropriate ways. Accordingly, the terms "neighbor," "neighboring," and "neighbors," as used herein to describe a sensor 90 with respect to another sensor 88, mean that the sensor 90 is within the neighborhood 100 of the other sensor 88. That is, sensor 90 neighbors/is a neighbor of sensor 88 if sensor 90 is within sensor 88's neighborhood 100.

As will be understood, embodiments of the system 10 take advantage of the spatially slowly changing nature of the dataset 74, i.e., the tendency of neighboring sensors 24 to have similar PET event counts, by looking for outlying/anomalous data 82 within the dataset 74 to determine the likelihood that a particular sensor 24 has failed.

As will be explained in greater detail below, the dataset 74 may be transformed into one or more two-dimensional ("2D") maps which may be organized so as to retain the neighborhoods 100 of the sensors 24. For example, in embodiments, the count statistics of sensors 24 disposed around the ring 92 at a given axial location may be plotted on a single row, while sensors 24 located along the axial direction may be plotted on a single column. As will be appreciated, the values across the locations within such 2D maps tend to be smoothly varying, with sudden changes in value indicating likely abnormalities in the corresponding sensors 24.

Figure 6:
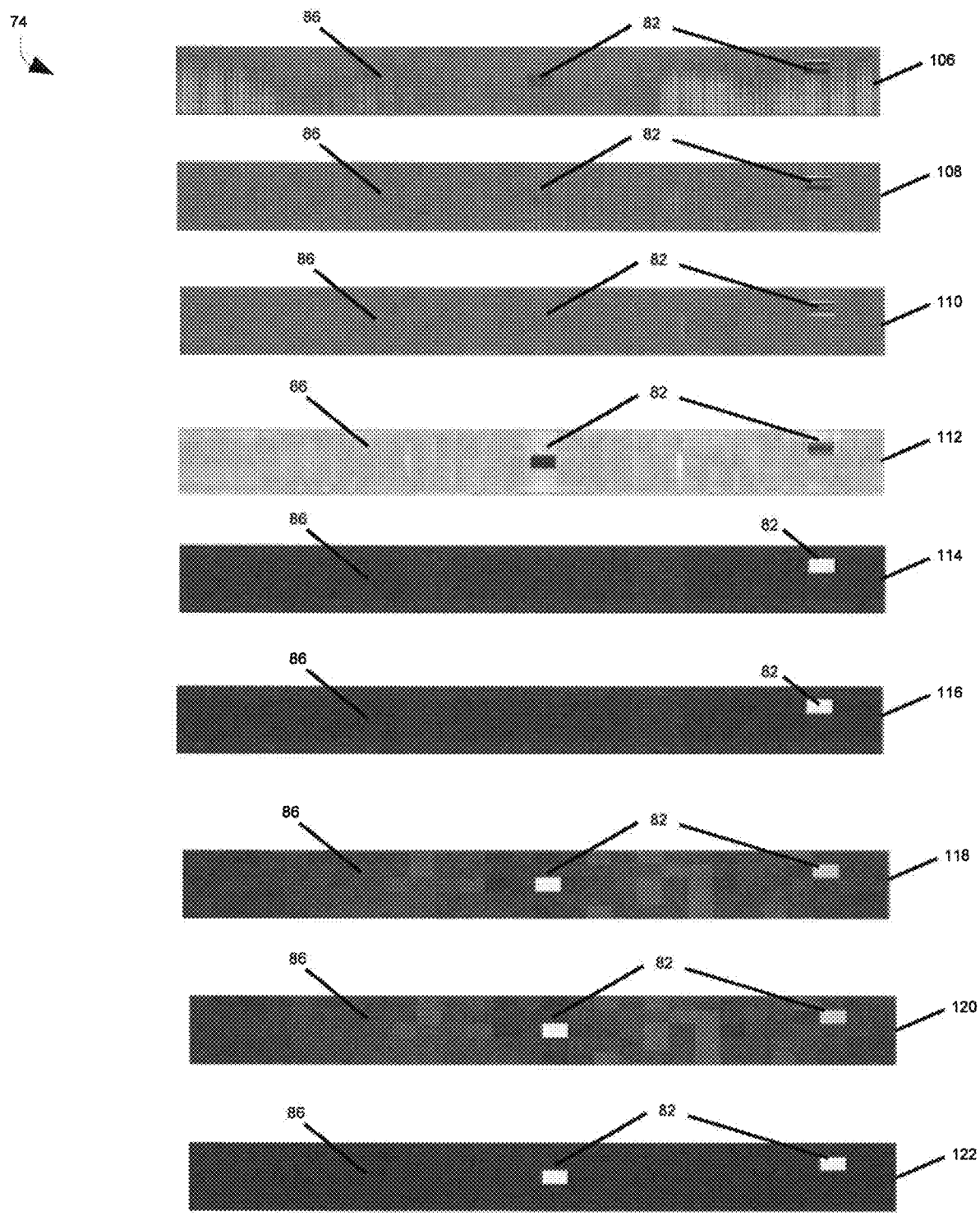
FIG. 6 is a diagram of one or more maps derived from a dataset acquired by the system of FIG. 1, in accordance with an embodiment of the present invention.
Figure 7:
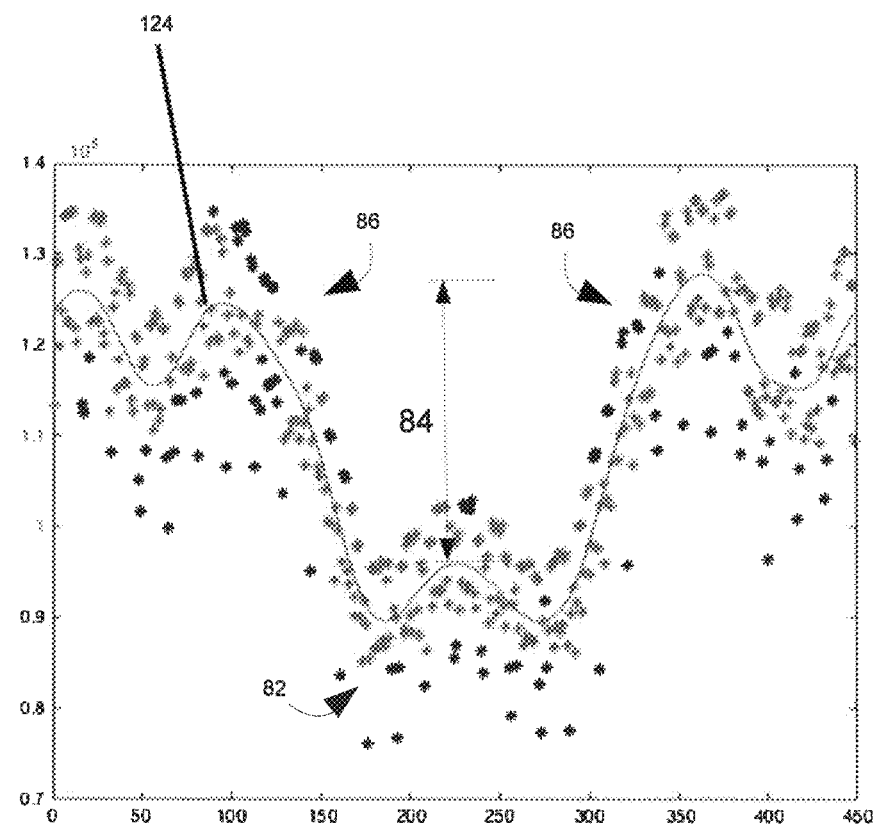
FIG. 7 is a graphical chart that depicts the normalization of a dataset acquired by the system of FIG. 1, in accordance with an embodiment of the present invention.

For example, illustrated in FIG. 6 is a singles/sensor map 106 in accordance with an embodiment of the invention, and its derived detrended map 108, normalized map 110, device map 112, Z map 114, significant Z map 116, edge difference map 118, significant edge map 120, and bad unit map 122. As will be understood, in embodiments, detecting 80 (FIG. 3) the anomalous data 82 may include constructing map 106 from the dataset 74 and fitting a smooth spline curve 124 (FIG. 7) to the row and column sums of the dataset 74 to generate the detrended map 108. In other words, the coincidence counts of the sensors 24 pairs in the dataset 74 are normalized so as to become detrended. Each unit 98 (FIG. 5) may then be divided by an average unit map, e.g., a map of 9×16 sensors 24 (FIG. 5) so as to remove variations due to difference in sensor 24 sensitivity depending from position within a unit 98, i.e., self-normalized. The z-map 114 may then be generated by taking the standard deviation of the detrended and normalized counts of each unit 98. The sum of counts for each row and column in a unit 98 of a device map 112 are then determined, and a neighbor map may be generated by taking the edge difference for counts in each unit map relative to its neighbors, e.g., four (4) neighbors for units in middle rows, and three (3) neighbors for units on the edge. An edge map 118 is then generated by finding the maximum difference, and normalizing by the expected counts in the unit 98. The standard deviation of the values of the edge map 118 and the z-map 114 may then be computed.

Next, outliers may be searched for by selecting elements within the maps that are more than a certain number of standard deviations from the mean. The outliers may then be removed so that the standard deviation of the remaining elements may be recomputed. As will be appreciated, the searching/removing of the outliers, and the computation of the standard deviation of the remaining elements may be repeated in an iterative manner, referred to herein as "significant z-processing," until new outliers are no longer found.

After the completion of significant z-processing, elements that fall outside of a predetermined threshold may be found for both the neighbor difference and the z map 114. As will be appreciated, this may generate two masks: M1 and M3, where elements are =1 if the corresponding unit 98 is an outlier. Each neighbor difference may then be checked to see if it is greater than some practical threshold, e.g., mask M2, =1 if difference is significant. Thus, the final expression for outliers may be given by (M1&&M2)||M3. Accordingly, as shown above, anomalous data 82 may initially be considered merely "suspect data" if its statistical difference 84 with respect to the reference data 86 exceeds an initial threshold, and then subsequently classified as "faulty data" if the statistical difference 84 exceed a subsequent threshold beyond the initial threshold. Further, while the above method of detecting outliers was described on a per/unit 98 basis, is should be understood that other groupings of sensors, e.g., modules, blocks, etc., may be used.

Returning back to FIG. 3, in embodiments, the method 76 may further include reconstructing 130 the image of the object 12 based at least in part on the dataset 74. As will be appreciated, in embodiments, the anomalous data 82 may contribute less to the reconstructed image than the reference data 86. For example, and as explained in greater detail below, in embodiments, the anomalous data 82 does not contribute to the reconstructed image. Further, reconstruction 130 of the image may include applying 132 a scattering model to the dataset 74 where the scattering model includes a scaling process that determines an amplitude of a scatter contribution of the scattering model while ignoring LORs 134 (FIG. 8) corresponding to sensors 88 identified/determined to have failed. In embodiments, the scaling process may be "tail scaling" such that, when data from a sensor 24 is not available, the corresponding "scatter tail" data is also missing.

For example, in embodiments, reconstruction 130 of the image may be accomplished via Ordered Subset Expectation Maximization ("OSEM") with an image update equation of:

$$\hat{f}_j^{(n+1)} = \frac{\hat{f}_j^{(n)}}{\sum_{i' \in s} H_{i'j}} \sum_{i \in s} H_{ij} \frac{p_i}{\sum_k H_{i'j} \hat{f}_k^{(n)}}$$

where $\hat{f}_j^{(n+1)}$ the next estimate of voxel j based on the current voxel estimate $\hat{f}_j^{(n)}$, S represents the projection subsets, p represents the measured data, $H_{ij}$ are the elements of the system model H and represent the probability that an emission from voxel j is detected in projection, or LOR, i. As will be appreciated, the system model accounts for factors of detector geometry, normalization, point spread function, and/or attenuation. As such, expectation maximization may be performed by forwarding projection $\hat{f}_j^{(n)}$ into the projection (sinogram) domain by multiplying it with elements $H_{ij}$. The ratio of the measured data $p_i$ may then be taken with the projection of the current voxel estimate. Next, the resulting ratio for the projections i in subset S may be backprojected into the image domain to obtain an update factor for the current voxel estimate. The update factor may then be multiplied with the current estimate and divided by a weighting term based on the system model. The above process may be repeated until convergence and/or for a preset/specified number of iterations.

Figure 8:
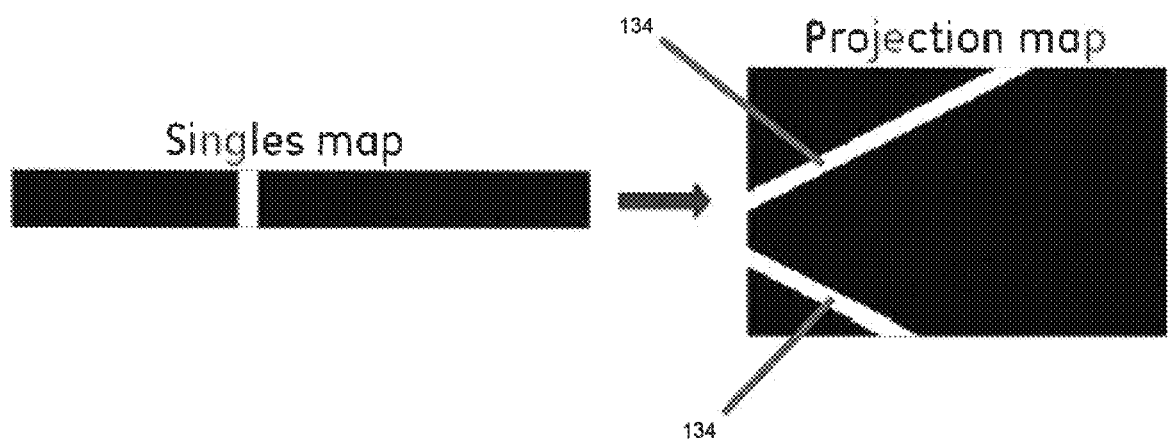
FIG. 8 is a diagram that depicts a scattering model utilized by the system of FIG. 1, in accordance with an embodiment of the present invention.

As will be understood, embodiments of the above resilient reconstruction may rely on the weighting of measured data based on the description of the system model. Thus, the weighting term in such embodiments indicates confidence in the data being backprojected. Therefore, a low value in the system matrix $H_{ij}$ gives a smaller weight of the corresponding projection i in the measured data $p_i$ on image voxel j, while a larger value will give $p_i$ a larger impact on voxel j. Thus, as will also be understood, by setting $H_{ij}$ equal to zero for the projections $p_i$ for detected anomalous data 82 acquired by failed sensors, e.g., sensor 88, the corresponding LORs are removed from the image update equation, thus minimizing the impact of the failed sensors on the reconstructed image. In other words, as shown in FIG. 8, in embodiments, the corresponding elements of the system matrix for sensors 88 that are detected 80 as having failed are set to zero (0) in order to remove them from consideration during reconstruction 130 of the image. Thus, when forward projecting an image, the zeros in the system matrix create zeros in the corresponding LORs in the sinogram.

Accordingly, in embodiments, the dataset 74 may be a singles histogram that is inspected to identify outlying PET events counts. As will be appreciated, such inspection may be performed on the dataset 74 in each PET imaging bad position, which in turn ensures that any intermittent sensors 24 are accounted for, even if they are not flagged during a daily quality assurance ("DQA") process/systems check. As will be understood, DQA system checks evaluate sensor 24 integrity so as to distinguish between general problems in sensor 24 calibration and inconsistent data from a few sensors 24 within a well-calibrated system. As such, in embodiments, the method of detecting 80 anomalous data 82 described above may be performed on DQA acquired data. Thus, if the system 10 fails conventional DQA criteria, but passes DQA when one or more sensors 24, e.g., five (5), are excluded, further scanning via the system 10 may be permitted.

Further, in embodiments, the method 76 may also include generating 136 a notification, e.g., e-mail, sms message, computer popup, audio/visual alarm, etc., that includes an indication/indicator that the first sensor 88 has acquired anomalous data 82. In other words, when the system 10 determines that the statistical difference between the anomalous data 82 and the reference data 84 indicates a high likelihood that one or more sensors 88 have failed, a message may be generated by the controller 16 and sent to appropriate repair personnel, and/or technologist operating the system 10.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. Thus, embodiments of the present invention may perform the methods disclosed herein in real-time. The term "computer-readable medium," as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, solid state drive (SSD), magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a method for performing fault-tolerant reconstruction of an image of an object is provided. The method includes acquiring a dataset corresponding to the object via a plurality of sensors, and detecting anomalous data within the dataset based at least in part on a statistical difference between the anomalous data and reference data within the dataset. The anomalous data is acquired by at least a first sensor of the plurality, and the reference data is acquired by at least a second sensor of the plurality that neighbors the first sensor. In certain embodiments, the method further includes reconstructing the image based at least in part on the dataset. In such embodiments, the anomalous data contributes less to the reconstructed image than the reference data. In certain embodiments, the anomalous data does not contribute to the reconstructed image. In certain embodiments, reconstructing the image based at least in part on the dataset includes applying a scattering model to the dataset. In such embodiments, a scaling process of the scattering model that determines an amplitude of a scatter contribution of the scattering model ignores lines of response corresponding to the first sensor. In certain embodiments, the statistical difference exceeds an initial threshold. In certain embodiments, the statistical difference exceeds a subsequent threshold beyond the initial threshold. In certain embodiments, the dataset corresponds to positron emissions from the object. In certain embodiments, the dataset includes at least one of a coincidence count detector map, a singles map, a coincidence-qualified singles count detector map, and a block busy map. In certain embodiments, the coincidence count detector map has a plurality of indices each corresponding to a coincidence count for a different combination of sensors of the plurality. In certain embodiments, the coincidence count is a total coincidence count for an imaging scan during which the dataset is acquired. In certain embodiments, the method further includes generating a notification that includes an indication that the first sensor has acquired the anomalous data.

Yet other embodiments provide for a system for performing fault-tolerant reconstruction of an image of an object. The system includes a plurality of sensors and a controller. The plurality of sensors is operative to acquire a dataset corresponding to the object. The controller is in electronic communication with the plurality of sensors and operative to detect anomalous data within the dataset based at least in part on a statistical difference between the anomalous data and reference data within the dataset. The anomalous data is acquired by at least a first sensor of the plurality, and the reference data is acquired by at least a second sensor of the plurality that neighbors the first sensor. In certain embodiments, the controller is further operative to reconstruct the image based at least in part on the dataset. In such embodiments, the anomalous data contributes less to the reconstructed image than the reference data. In certain embodiments, the anomalous data does not contribute to the reconstructed image. In certain embodiments, the controller is further operative to reconstruct the image by applying a scattering model to the dataset. In such embodiments, a scaling process of the scattering model that determines an amplitude of a scatter contribution of the scattering model ignores lines of response corresponding to the first sensor. In certain embodiments, the statistical difference exceeds an initial threshold. In certain embodiments, the statistical difference exceeds a subsequent threshold beyond the initial threshold. In certain embodiments, the dataset includes at least one of a coincidence count detector map, a singles map, a coincidence-qualified singles count detector map, and a block busy map. In certain embodiments, the coincidence count detector map has a plurality of indices each corresponding to a coincidence count for a different combination of sensors of the plurality. In certain embodiments, the coincidence count is a total coincidence count for an imaging scan during which the dataset is acquired. In certain embodiments, the controller is further operative to generate a notification that includes an indication that the first sensor has acquired the anomalous data.

Yet still other embodiments provide for a non-transitory computer readable medium storing instructions. The stored instructions are configured to adapt a controller to detect anomalous data within a dataset based at least in part on a statistical difference between the anomalous data and reference data within the dataset. The dataset corresponds to an object and is acquired by a plurality of sensors. The anomalous data is acquired by at least a first sensor of the plurality, and the reference data is acquired by at least a second sensor of the plurality that neighbors the first sensor. In certain embodiments, the stored instructions are further configured to adapt the controller to reconstruct the image based at least in part on the dataset. In such embodiments, the anomalous data contributes less to the reconstructed image than the reference data. In certain embodiments, the anomalous data does not contribute to the reconstructed image. In certain embodiments, the controller reconstructs the image by applying a scattering model to the dataset. In such embodiments, a scaling process of the scattering model that determines an amplitude of a scatter contribution of the scattering model ignores lines of response corresponding to the first sensor. In certain embodiments, the statistical difference exceeds an initial threshold. In certain embodiments, the statistical difference exceeds a subsequent threshold beyond the initial threshold. In certain embodiments, the dataset includes at least one of a coincidence count detector map, a singles map, a coincidence-qualified singles count detector map, and a block busy map. In certain embodiments, the coincidence count detector map has a plurality of indices each corresponding to a coincidence count for a different combination of sensors of the plurality. In certain embodiments, the coincidence count is a total coincidence count for an imaging scan during which the dataset is acquired. In certain embodiments, the stored instructions are further configured to adapt the controller to generate a notification that includes an indication that the first sensor has acquired the anomalous data.

Accordingly, by detecting failed sensors by comparing PET data acquired by a sensor to PET data acquired by neighboring sensors, some embodiments of the present invention may provide for the detection and correction of a wider variety of PET sensor failures than currently provided by prior art PET systems. In other words, and as described above, some embodiments of the present invention take advantage of the spatially slowly changing nature of acquired PET data, i.e., the tendency of neighboring sensors to have similar PET event counts, by looking for outlying/anomalous data within an acquired PET dataset to determine the likelihood that a particular sensor has failed.

Thus, unlike traditional PET systems, some embodiments of the present invention provide for the ability to detect failed sensors without requiring the PET data to be acquired and/or formatted in accordance with List Mode. As such, by detecting anomalous data within each acquired dataset, some embodiments may provide for the detection of intermittent sensor failures that typically go undetected by traditional DQA system checks. Therefore, some embodiments of the present invention provide for the ability to detect and to correct for a wider variety of sensor failures than many traditional PET systems.

Further, by generating a notification message for maintenance personnel that identifies one or more failed PET sensors, some embodiments of the present invention provide for improved diagnostic and repair times, and/or reduced maintenance costs. For example, some embodiments may prevent scenarios in which a patient is injected with a radionuclide-labeled agent only to be prevented from completing a PET scan due to a failed sensor.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A method for performing fault-tolerant reconstruction of an image of an object comprising:
   acquiring a dataset corresponding to the object via a plurality of sensors;
   detecting anomalous data within the dataset based at least in part on a statistical difference between the anomalous data and reference data within the dataset; and
   reconstructing the image based at least in part on the dataset;
   wherein:
      the anomalous data contributes a non-zero amount to the reconstructed image that is less than an amount contributed to the reconstructed image by the reference data, and
      the anomalous data is acquired by at least a first sensor of the plurality, and the reference data is acquired by at least a second sensor of the plurality that neighbors the first sensor.

2. The method of claim 1, wherein reconstructing the image based at least in part on the dataset comprises:
   applying a scattering model to the dataset; and
   wherein a scaling process of the scattering model that determines an amplitude of a scatter contribution of the scattering model ignores lines of response corresponding to the first sensor.

3. The method of claim 1, wherein the statistical difference exceeds an initial threshold.

4. The method of claim 3, wherein the statistical difference exceeds a subsequent threshold beyond the initial threshold.

5. The method of claim 1, wherein the dataset corresponds to positron emissions from the object.

6. The method of claim 5, wherein the dataset comprises at least one of a coincidence count detector map, a singles map, a coincidence-qualified singles count detector map, and a block busy map.

7. The method of claim 6, wherein the coincidence count detector map has a plurality of indices each corresponding to a coincidence count for a different combination of sensors of the plurality.

8. The method of claim 7, wherein the coincidence count is a total coincidence count for an image frame during which the dataset is acquired.

9. The method of claim 1 further comprising:
   generating a notification that includes an indication that the first sensor has acquired the anomalous data.

10. A system for performing fault-tolerant reconstruction of an image of an object comprising:
    a plurality of sensors operative to acquire a dataset corresponding to the object;
    a controller in electronic communication with the plurality of sensors and operative to detect anomalous data within the dataset based at least in part on a statistical difference between the anomalous data and reference data within the dataset, wherein the detecting anomalous data includes transforming the dataset to a two-dimensional map configured to retain neighborhoods of each sensor of the plurality of sensors; and generating a detrended map from the two-dimensional map; and
    wherein:
       the controller is further operative to reconstruct the image based at least in part on the dataset;
       the anomalous data contributes a non-zero amount to the reconstructed image that is less than an amount contributed to the reconstructed image by the reference data; and
       the anomalous data is acquired by at least a first sensor of the plurality, and the reference data is acquired by at least a second sensor of the plurality that neighbors the first sensor.

11. The system of claim 10, wherein the controller is further operative to reconstruct the image by applying a scattering model to the dataset; and
    wherein a scaling process of the scattering model that determines an amplitude of a scatter contribution of the scattering model ignores lines of response corresponding to the first sensor.

12. The system of claim 10, wherein the statistical difference exceeds an initial threshold.

13. The system of claim 12, wherein the statistical difference exceeds a subsequent threshold beyond the initial threshold.

14. The system of claim 10, wherein the dataset comprises at least one of a coincidence count detector map, a singles map, a coincidence-qualified singles count detector map, and a block busy map.

15. The system of claim 14, wherein the coincidence count detector map has a plurality of indices each corresponding to a coincidence count for a different combination of sensors of the plurality.

16. A non-transitory computer readable medium storing instructions configured to adapt a controller to:
    detect anomalous data within a dataset based at least in part on a statistical difference between the anomalous data and reference data within the dataset, the dataset corresponding to an object and acquired by a plurality of sensors; and
    reconstruct an image based at least in part on the dataset;
    wherein:
       the anomalous data contributes a non-zero amount to the reconstructed image that is less than an amount contributed to the reconstructed image by the reference data; and
    the anomalous data is acquired by at least a first sensor of the plurality, and the reference data is acquired by at least a second sensor of the plurality that neighbors the first sensor.

17. The system of claim 10, wherein:
    generating the detrended map includes fitting a smooth spline curve to row and column sums of the dataset.

* * * * *